United States Patent
Herkelmann et al.

(12)

(10) Patent No.: US 6,294,055 B2
(45) Date of Patent: *Sep. 25, 2001

(54) PROCESS FOR THE SEPARATION OF HYDROGEN FLUORIDE FROM ITS MIXTURES WITH A HYDROFLUOROALKANE CONTAINING FROM 3 TO 6 CARBON ATOMS

(75) Inventors: Ralf Herkelmann, Bad Rappenau; Carsten Brosch, Hannover, both of (DE); Vincent Wilmet, Wavre (BE)

(73) Assignee: Solvay S.A., Brussels (BE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/152,111

(22) Filed: Sep. 11, 1998

(30) Foreign Application Priority Data

Sep. 24, 1997 (FR) .................................................. 97.11975

(51) Int. Cl.⁷ ............................. B01D 3/34; C07C 17/38; C07C 17/383; C01B 7/19
(52) U.S. Cl. ................................ 203/43; 203/44; 203/45; 203/46; 423/483; 570/178; 570/180
(58) Field of Search ................................ 203/49, 43, 44, 203/45, 67, 73, 46; 570/177, 178, 180; 423/484, 488, 483

(56) References Cited

U.S. PATENT DOCUMENTS

| 2,450,414 | * | 10/1948 | Benning ................................ 203/73 |
| 2,640,086 | * | 5/1953 | Baldwin ............................... 570/165 |
| 3,947,558 | * | 3/1976 | Van Eijl ................................ 203/80 |
| 4,209,470 | * | 6/1980 | Lorquet ................................ 423/240 |
| 5,094,773 | * | 3/1992 | Manzer et al. ........................ 570/178 |
| 5,196,616 | * | 3/1993 | Lee et al. .............................. 570/178 |
| 5,426,254 | | 6/1995 | Galland et al. . |
| 5,523,015 | * | 6/1996 | Tsuda et al. ........................... 203/50 |
| 5,560,899 | * | 10/1996 | Solinas et al. ........................ 423/484 |
| 5,574,192 | * | 11/1996 | Van der Puy et al. ............... 570/167 |
| 5,718,807 | * | 2/1998 | Miller et al. ........................... 203/67 |
| 5,739,406 | | 4/1998 | Pennetreau . |
| 6,040,487 | | 3/2000 | Baker et al. .......................... 570/172 |
| 6,120,652 | * | 9/2000 | Hibino et al. .......................... 203/51 |

FOREIGN PATENT DOCUMENTS

| 0588676A1 | 3/1994 | (EP) . |
| 0601373A1 | 6/1994 | (EP) . |
| 0699649A1 | 3/1996 | (EP) . |
| 74045842 | 12/1974 | (JP) . |
| 09110738 | 4/1997 | (JP) . |
| 10/017501 | 1/1998 | (JP) . |
| 9705089 | * 2/1997 | (WO) . |
| 97/05089 | 2/1997 | (WO) . |
| 97/13719 | 4/1997 | (WO) . |
| 97/15540 | 5/1997 | (WO) . |
| 97/49656 | 12/1997 | (WO) . |
| 96/8481 | 7/1997 | (ZA) . |

* cited by examiner

Primary Examiner—Virginia Manoharan
(74) Attorney, Agent, or Firm—Venable; Marina V. Schneller

(57) ABSTRACT

Process for the separation of hydrogen fluoride from its mixtures with a hydrofluoroalkane containing from 3 to 6 carbon atoms, by extraction using an organic solvent.

24 Claims, No Drawings

PROCESS FOR THE SEPARATION OF HYDROGEN FLUORIDE FROM ITS MIXTURES WITH A HYDROFLUOROALKANE CONTAINING FROM 3 TO 6 CARBON ATOMS

The present invention relates to a process for the separation of hydrogen fluoride from its mixtures with a hydrofluoroalkane containing from 3 to 6 carbon atoms.

Hydrofluoroalkanes can be prepared by reaction of a suitable chloro precursor with hydrogen fluoride, as disclosed, for example, in patent applications EP-A1-0,699,649 and WO-A1-97/15540 (in the name of Solvay) and in patent application WO-A1-97/05089. In such a process, on leaving the hydrofluorination reactor, the mixture of reaction products contains, besides the desired hydrofluoroalkane, hydrogen chloride originating from the elimination of the chlorine atom(s) from the starting chloro precursor, hydrogen fluoride and unconverted chloro precursor, optionally inert diluents, as well as low amounts of various by-products. Given that the process is usually performed with an excess of hydrogen fluoride relative to the chloro precursor, unconverted hydrogen fluoride usually remains in the mixture of reaction products. Although most of the constituents of the mixture of reaction products can readily be separated out completely by distillation, a complete separation between the hydrogen fluoride and the hydrofluoroalkane is generally very difficult to achieve by distillation, since these compounds often form azeotropic mixtures.

Patent application WO-A1-97/05089 discloses, inter alia, a process for the purification of hydro(chloro)fluoroalkanes (in particular 1,1,1,3,3-pentafluoropropane or HFC-245fa) from azeotropic mixtures with hydrogen fluoride, by a technique of azeotropic distillation comprising two successive steps of distillation at different temperatures and pressures.

However, this azeotropic distillation technique has the drawbacks of requiring a large temperature or pressure difference between the two columns, so as to have a sufficient separation potential (difference in composition between the azeotrope at low pressure/temperature and the azeotrope at high pressure/temperature) and to give rise to a large circulation flow rate between the two columns.

Patent application WO-A1-97/13719 discloses a process for the separation and recovery of hydrogen fluoride from its mixtures (azeotropic) with, inter alia, hydrofluoroalkanes containing from 1 to 6 carbon atoms (in particular HFC-245fa). The mixture is placed in contact with a solution of alkali metal fluoride (in particular potassium or caesium fluoride) and the organic phase is separated from the phase containing the hydrogen fluoride and the alkali metal fluoride.

Using this known process, there may be fear of contaminating the organic phase with the potassium or caesium fluoride and the risk of decomposing the hydrofluoroalkanes which this contamination might entail. Moreover, these alkali metal fluorides, and more particularly caesium fluoride, are very expensive.

The object of the present invention is to provide a process for the separation of hydrogen fluoride from its mixtures with a hydrofluoroalkane containing from 3 to 6 carbon atoms, which does not have the drawbacks of the abovementioned processes.

To this end, the invention relates to a process for the separation of hydrogen fluoride from its mixtures with at least one hydrofluoroalkane containing from 3 to 6 carbon atoms, according to which the separation is carried out by extraction using at least one organic solvent.

The organic solvent can be a halo or non-halo compound.

As examples of non-halo organic solvents, mention may be made of hydrocarbons containing from 5 to 10 carbon atoms, in particular n-pentane, n-hexane, n-heptane and n-octane.

Examples of halo-organic solvents are chloroform, trichloroethylene, tetrachloroethylene, tetrachloromethane, 1,2-dichloroethane, 1,1,1-trichloroethane, 1,1,2-trichloroethane, 1,1-dichloro-1-fluoroethane (HCFC-141b), 1,1,1- or 1,1,2-trifluorotrichloroethane, 1,2,3-trichloropropane, perfluorohydrocarbons, bromobenzene, o-dichlorobenzene, p-chlorotoluene, p-chlorotrifluorobenzene and 1,2-dichloro-4-trifluorobenzene, as well as mixtures of these compounds.

In particular, when the process is applied to the separation of the hydrogen fluoride/1,1,1,3,3-pentafluorobutane (HFC-365mfc) mixture, the preferred extraction solvents are bromobenzene, o-dichlorobenzene and tetrachloroethylene. Bromobenzene and o-dichlorobenzene are particularly preferred.

The expression "hydrofluoroalkane containing from 3 to 6 carbon atoms" is understood to denote the hydrofluoroalkanes corresponding to the general formula $C_aH_{(2a+2)-b}F_b$ in which a=3 to 6 and b=1 to 2a+1. The hydrofluoroalkanes corresponding to the general formula $C_aH_{(2a+2)-b}F_b$ in which a=3 to 4 and b=5 to 2a+1 are preferred.

As examples of hydrofluoroalkanes containing from 3 to 6 carbon atoms which can be separated from their mixtures with hydrogen fluoride by the process according to the invention, mention may be made of 1,1,1,3,3-pentafluoropropane (HFC-245fa), 1,1,2,2,3-pentafluoropropane (HFC-245ca), 1,1,1,2,3-pentafluoropropane (HFC-245eb), 1,1,1,3,3,3-hexafluoropropane (HFC-236fa), 1,1,1,2,3,3-hexafluoropropane (HFC-236ea), 1,1,1,2,3,3,3-heptafluoropropane (HFC-227ea), 1,1,1,3,3-pentafluoro-2-methylpropane (HFC-365mps), 1,1,1,3,3-pentafluorobutane (HFC-365mfc), 1,1,1,4,4,4-hexafluorobutane (HFC-356mff) and, 1,1,1,2,3,4,4,5,5,5-decafluoropentane (HFC-43-10mee). Compounds containing from 3 to 4 carbon atoms are preferred. 1,1,1,3,3-Pentafluoropropane (HFC-245fa) and 1,1,1,3,3-pentafluorobutane (HFC-365mfc) are particularly preferred.

The weight ratio of the hydrogen fluoride to the hydrofluoroalkane depends on the amount of hydrogen fluoride used in the hydrofluorination step of the process for the synthesis of the hydrofluoroalkane. In general, the hydrogen fluoride is in excess relative to the hydrofluoroalkane.

The extraction is preferably carried out on a mixture which has a hydrogen fluoride/hydrofluoroalkane weight ratio close to that of the azeotropic composition. If the initial mixture of hydrogen fluoride and hydrofluoroalkane differs from that in the azeotropic composition, it may be advantageous to carry out a predistillation in order to separate the HF/HFC azeotrope from the excess compound (HF or HFC). The azeotropic composition is then subjected to extraction.

In the separation process according to the invention, the weight ratio of the organic solvent to the mixture of hydrogen fluoride and hydrofluoroalkane is generally at least 0.1. Preferably, the process is performed with a weight ratio of at least 0.2. The weight ratio of the organic solvent to the mixture of hydrogen fluoride and hydrofluoroalkane does not generally exceed 10. Preferably, it does not exceed 5.

The temperature at which the extraction is carried out is generally at least −25° C. Preferably, it is about −10° C. The temperature generally does not exceed 40° C. Preferably, it does not exceed 30° C.

The process according to the invention is carried out at a pressure which is sufficient to keep the mixture in the liquid state. It can be carried out under the autogenous pressure of the mixture; in this case, the pressure is generally less than 3 bar. Alternatively, it can be carried out at a pressure above the autogenous pressure of the mixture by introducing an inert gas. In this case, the total pressure will generally be less than 10 bar; preferably, the pressure used will be less than 3 bar but greater than 1 bar. Any gaseous substance which does not react substantially under the extraction conditions, such as nitrogen, hydrogen chloride, argon or a mixture thereof, will be used as inert gas. Preferably, nitrogen will be used.

The mixture of hydrogen fluoride and hydrofluoroalkane is placed in contact with the organic extraction solvent in one or more steps, using any conventional liquid-liquid extraction device, for example by placing in intimate contact using a static mixer, a stirred reactor, a rotary-disc extractor, an extractor with centrifugation or a column with perforated plates, operating either counter-currentwise or co-currentwise. Preferably, the placing in contact is carried out in a stirred reactor. The extraction can be performed in a continuous or batchwise manner. Preferably, it is performed continuously.

After extraction, an organic phase enriched with hydrofluoroalkane is separated from a phase enriched with hydrogen fluoride (referred to hereinbelow as HF phase). This separation can be carried out simply by separation by settling, but it is also possible to use any other standard device for phase separation, such as a centrifugation or a separation by hydrocyclone. Separation by settling is preferred.

The organic phase mainly comprises the extraction solvent enriched with hydrofluoroalkane, but can also contain a certain amount of hydrogen fluoride. Its composition usually corresponds to the equilibrium composition, determined by the partition coefficients of the various compounds between the hydrogen fluoride and the extraction solvent.

The hydrofluoroalkane can be readily separated from the other constituents of the organic phase by means of a standard separation technique such as a distillation. The hydrofluoroalkane can then be treated via a wet route in order to remove the last traces of acidity and/or adsorbed onto active charcoal and/or deacidified on zeolite or alumina. The solvent can be recycled into the extraction step.

The HF phase mainly contains hydrofluoroalkane depleted hydrogen fluoride, but can also contain an appreciable amount of extraction solvent.

When the extraction solvent is inert under the reaction conditions, the HF phase can be conveyed, as it is, directly to the hydrofluorination reactor for the production of hydrofluoroalkane.

According to another embodiment of the process, the HF phase can advantageously be subjected to a suitable treatment, such as a distillation, which makes it possible to recover hydrogen fluoride virtually freed of solvent at the column head, which is recycled into the reactor, and solvent at the foot of the column, which is recycled into the extraction step.

The examples which follow are intended to illustrate the present invention without, however, limiting its scope.

EXAMPLES 1 to 11

A mixture of 1,1,1,3,3-pentafluorobutane (HFC-365mfc) and of HF which is close to the azeotropic composition was introduced into a 0.5 l "INOX 316" stainless steel autoclave equipped with a paddle stirrer, two dip tubes, to allow samples of the two liquid phases to be removed (at the bottom and at the top of the reactor), and a finger fitted with a thermocouple, to allow the temperature to be measured, and this mixture was extracted using a solvent. The solvent used and the amounts by weight of HFC-365mfc, of HF and of solvent used are given in Table I. The autoclave is immersed in a bath maintained at constant temperature. The extraction was carried out at −10° C. under an autogenous pressure, i.e. slightly less than 1 bar. The mixture was stirred for 1 hour (Example 10), 4 hours (Ex. 1 to 5 and 8) or 24 hours (Ex. 6, 7, 9 and 11) and was then left to separate by settling for at least 1 hour.

For each example, the extraction efficacy was evaluated after taking samples from each of the two liquid phases. These liquid samplings were carried out via a lock chamber of about 5 cm$^3$ after pressurizing the autoclave under 2 bar of nitrogen. The samples of liquid taken from the HF phase were then depressurized in a vessel containing a supply of ethanol. The HF content was assayed on this ethanolic solution diluted with water (about 100 times) using a specific electrode. As regards the organic phase, its composition was determined by gas-chromatographic analysis after neutralization of the hydrogen fluoride with lime. The results of these analyses are given in Table I.

TABLE I

| Ex. | Solvent | Starting composition (g) | | | Starting HFC/HR | Composition of the organic phase (% by weight) | | | HFC/HF in the organic phase |
|---|---|---|---|---|---|---|---|---|---|
| | | HFC | HF | solv. | (g/g) | HFC | HF | solv. | (g/g) |
| 1 | tetrachloroethylene | 130 | 93 | 102 | 1.4 | 11.8 | — | 88.2 | — |
| 2 | tetrachloroethylene | 101 | 93 | 100 | 1.1 | 9.3 | 0.1 | 90.6 | 93.0 |
| 3 | trichloroethylene | 101 | 116 | 100 | 0.9 | 34.2 | 0.4 | 65.4 | 85.5 |
| 4 | 1,2-dichloroethane | 98 | 102 | 99 | 1.0 | 39.3 | 2.8 | 57.9 | 14.0 |
| 5 | 1,1,2-trichloroethane | 96 | 106 | 99 | 0.9 | 39.0 | 1.1 | 59.9 | 35.5 |
| 6 | tetrachloromethane | 96 | 92 | 95 | 1.0 | 34.2 | 0.8 | 65.0 | 42.8 |
| 7 | tetrachloromethane | 100 | 93 | 103 | 1.1 | 29.7 | 0.4 | 69.9 | 74.3 |
| 8 | 1,2,3-trichloropropane | 106 | 109 | 103 | 1.0 | 32.3 | 1.9 | 65.8 | 17.0 |
| 9 | o-dichlorobenzene | 100 | 92 | 101 | 1.1 | 31.5 | 0.2 | 68.2 | 157.5 |

TABLE I-continued

| Ex. | Solvent | Starting composition (g) | | | Starting HFC/HR (g/g) | Composition of the organic phase (% by weight) | | | HFC/HF in the organic phase (g/g) |
|---|---|---|---|---|---|---|---|---|---|
| | | HFC | HF | solv. | | HFC | HF | solv. | |
| 10 | bromobenzene | 101 | 102 | 152 | 1.0 | 21.7 | 0.2 | 78.1 | 108.5 |
| 11 | n-octane | 101 | 102 | 102 | 1.0 | 15.0 | 0.7 | 84.3 | 21.4 |

The results of Table I show that the concentration of 1,1,1,3,3-pentafluorobutane (HFC-365mfc) in the organic phase ranges from about 9% by weight in the case of tetrachloroethylene up to 30 to 40% by weight for the other solvents.

The concentration of hydrogen fluoride in the organic phase is lowest in the case of tetrachloroethylene.

The solvents with which the highest HFC/HF ratio is obtained in the organic phase, i.e. solvents which make it possible to extract the maximum amount of 1,1,1,3,3-pentafluorobutane (HFC-365mfc) with the minimum amount of hydrogen fluoride, are o-dichlorobenzene, bromobenzene, tetrachloroethylene, trichloroethylene and tetrachloromethane.

EXAMPLES 12 and 13

The same procedure as in Examples 1 to 11 was applied to the extraction of the HF/1,1,1,3,3-pentafluoropropane (HFC-245fa) mixture with tetrachloroethylene and with o-dichlorobenzene, except that, in Example 12, the extraction was carried out at −12° C. and the mixture was stirred for 15 hours and was then left to separate by settling for 3 hours, and, in Example 13, the extraction was carried out at −70° C. and the mixture was stirred for 65 hours and was then left to separate by settling for 3 hours.

Samples of liquid were taken as in Examples 1 to 11, except that the samples of liquid taken in the lock chamber were depressurized in a vessel containing a mixture of water and tetrachloromethane. The composition of the organic phase present in the reactor was analysed. The results of these analyses are given in Table II.

TABLE II

| Ex. | Solvent | Starting composition (g) | | | Starting HFC/HF (g/g) | Composition of the organic phase (*) (% by weight) | | | HFC/HF in the organic phase (g/g) |
|---|---|---|---|---|---|---|---|---|---|
| | | HFC | HF | solv. | | HFC | HF | solv. | |
| 12 | tetrachloroethylene | 67.5 | 90.2 | 161.0 | 0.75 | 3.75 | 0.17 | 96.1 | 22.1 |
| 13 | o-dichlorobenzene | 101.1 | 102.3 | 128.7 | 0.99 | 9.5 | 0.2 | 90.3 | 47.5 |

(*) present in the reactor

What is claimed is:

1. A process for the separation of hydrogen fluoride from a mixture comprising 1,1,1,3,3-pentafluorobutane and HF, wherein the process comprises extracting said mixture with at least one organic solvent, under conditions of pressure which is sufficient to maintain the mixture in a liquid state, wherein said pressure is the autogenous pressure of the mixture or a pressure less than 10 bars, to provide an organic phase enriched in 1,1,1,3,3-pentafluorobutane and a second phase enriched in hydrogen fluoride; and separating said organic phase enriched in 1,1,1,3,3-pentafluorobutane from said second phase enriched in hydrogen fluoride.

2. The process of claim 1, wherein the at least one organic solvent is a halogenated organic compound.

3. The process of claim 1, wherein the at least one organic solvent is selected from a group consisting of chloroform, trichloroethylene, tetrachloroethylene, tetrachloromethane, 1-2-dichloroethane, 1,1,1-trichloroethane, 1,1,2-trichloroethane, 1,1-dichloro-1-fluoroethane (HCFC-141b), 1,1,1- or 1,1,2-trifluorotrichloroethane, 1,2,3-trichloropropane, perfluorohydrocarbons, bromobenzene, o-dichlorobenzene, p-chlorotoluene, p-chlorotrifluorobenzene, 1,2-dichloro-4-trifluorobenzene, and mixtures of these compounds.

4. The process of claim 1, wherein the at least one organic solvent is selected from a group consisting of bromobenzene, o-dichlorobenzene and tetrachloroethylene.

5. The process of claim 1, wherein the at least one organic solvent is a hydrocarbon containing from 5 to 10 carbon atoms.

6. Process according to any of claims 1 through 5, wherein the ratio by weight between the at least one organic solvent and the hydrogen fluoride and 1,1,1,3,3-pentafluorobutane mixture is between 0.1 and 10.

7. The process of claim 1, wherein the extraction is carried out at a temperature of between −25° C. and 40° C.

8. The process of claim 1, wherein the extracting is carried out in the presence of an inert gas, and wherein the inert gas is nitrogen.

9. Process according to any of claims 1 through 7, wherein said extracting is followed by at least one distillation of the organic phase and/or of the second phase.

10. The process of claim 1, wherein the mixture comprises an azeotropic composition comprising hydrogen fluoride and pentafluorobutane.

11. The process of claim 1, which further comprises, after said extracting, recycling hydrogen fluoride to a reactor.

12. The process of claim 1, wherein said at least one organic solvent is a hydrocarbon containing from 5 to 10 carbon atoms.

13. A process for the separation of hydrogen fluoride from a mixture comprising HF and at least one hydrofluoroalkane selected from the group consisting of 1,1,1,3,3-pentafluoropropane (HFC-245fa), 1,1,2,2,3-pentafluoropropane (HFC-245ca), 1,1,1,2,3-pentafluoropropane (HFC-245eb), 1,1,1,3,3,3-hexafluoropropane (HFC-236fa), 1,1,1,2,3,3-hexafluoropropane (HFC-236ea) and 1,1,1,2,3,3,3-heptafluoropropane (HFC-227ea), wherein the process comprises extracting said mixture with at least one organic solvent, under conditions of pressure which is sufficient to maintain the mixture in a liquid sate, wherein said pressure is the autogenous pressure of the mixture or a pressure less than 10 bars, to provide an organic phase enriched in said at least one hydrofluoroalkane and a second phase enriched in hydrogen fluoride said at least one hydrofluoroalkane being selected from the group consisting of 1,1,1,3,3-pentafluoropropane (HFC-245fa), 1,1,2,2,3-pentafluoropropane (HFC-245ca), 1,1,1,2,3-pentafluoropropane (HFC-245eb), 1,1,1,3,3,3-hexafluoropropane (HFC-236fa), 1,1,1,2,3,3-hexafluoropropane (HFC-236ea) and 1,1,1,2,3,3,3-heptafluoropropane (HFC-227ea); and separating said organic phase enriched in said at least one hydrofluoroalkane from said second phase enriched in hydrogen fluoride.

14. The process of claim 13, wherein said at least one hydrofluoroalkane is 1,1,1,3,3-pentafluoropropane (HFC-245fa).

15. The process of claim 13, wherein said at least one hydrofluoroalkane is selected from the group consisting of 1,1,1,3,3,3-hexafluoropropane (HFC-236fa) and 1,1,1,2,3,3,3-heptafluoropropane (HFC-227ea).

16. The process of claim 13, wherein said at least one organic solvent is a halo-organic compound.

17. The process of claim 13, wherein said at least one organic solvent is selected from a group consisting of chloroform, trichloroethylene, tetrachloroethylene, tetrachloromethane, 1-2-dichloroethane, 1,1,1-trichloroethane, 1,1,2-trichloroethane, 1,1-dichloro-1-fluoroethane (HCFC-141b), 1,1,1- or 1,1,2-trifluorotrichloroethane, 1,2,3-trichloropropane, perfluorohydrocarbons, bromobenzene, o-dichlorobenzene, p-chlorotoluene, p-chlorotrifluorobenzene, 1,2-dichloro-4-trifluorobenzene, and mixtures of these compounds.

18. The process of claim 13, wherein said at least one organic solvent is selected from a group consisting of bromobenzene, o-dichlorobenzene and tetrachloroethylene.

19. The process of claim 13, wherein weight ratio of said at least one organic solvent to the mixture of hydrogen fluoride and said at least one hydrofluoroalkane is between 0.1 and 10.

20. The process of claim 13, wherein said extracting is carried out at a temperature of between −25° C. and 40° C.

21. The process of claim 13, wherein the extracting is carried out in the presence of an inert gas, and wherein the inert gas is nitrogen.

22. The process of claim 13, wherein said extracting is followed by at least one distillation of the organic phase and/or of the second phase.

23. The process of claim 13, wherein said extracting is carried out on a mixture which comprises an azeotropic composition which comprises hydrogen fluoride and said at least one hydrofluoroalkane.

24. The process of claim 13, which further comprises, after said extracting, recycling hydrogen fluoride to a reactor.

* * * * *